United States Patent [19]

Gracey et al.

[11] Patent Number: 5,097,089
[45] Date of Patent: Mar. 17, 1992

[54] SYNTHESIS OF GLYCEROL FROM FORMALDEHYDE

[75] Inventors: Benjamin P. Gracey; Barry Hudson; Peter S. Williams, all of North Humberside, England

[73] Assignee: BP Chemicals Limited, London, England

[21] Appl. No.: 501,366

[22] Filed: Mar. 27, 1990

Related U.S. Application Data

[63] Continuation of Ser. No. 236,651, Aug. 25, 1988, abandoned.

[30] Foreign Application Priority Data

Aug. 29, 1987 [GB] United Kingdom ............... 8720491

[51] Int. Cl.$^5$ ..................... C07C 29/145; C07C 31/22
[52] U.S. Cl. ..................... 568/863; 568/388
[58] Field of Search ........................... 568/863

[56] References Cited

U.S. PATENT DOCUMENTS

| | | | |
|---|---|---|---|
| 3,935,284 | 1/1976 | Kruse, I | 568/863 |
| 4,024,193 | 5/1977 | Kruse, II | 260/618 D |
| 4,247,653 | 1/1981 | Wagner | 568/863 |
| 4,341,909 | 7/1982 | Schneider et al. | 568/863 |
| 4,358,619 | 11/1982 | Stemmler et al. | 568/863 |

FOREIGN PATENT DOCUMENTS 0219317 4/1987 European Pat. Off. .
0245976 11/1987 European Pat. Off. .

OTHER PUBLICATIONS

Matsumoto et al., "J. Am. Chem. Soc.", vol. 106, No. 17, (1984) pp. 4829–4832.
Patent Abstracts of Japan, vol. 13, No. 293 (C-615) [3641], Jul. 6, 1989; & JP-A-185944.
Patent Abstracts of Japan, vol. 9, No. 17 (C-262) [1740], Jan. 24, 1985 & JP-A-59 164746, Sept. 17, 1984.
Patent Abstracts of Japan, vol. 9, No. 17 (C 262) [1740] Jan. 24, 1985 & JP-A-59 164 745, Sept. 17, 1984.
Chemical Abstracts, vol. 90, p. 539, 1979, Abstract No. 5845X T. A. Antonova et al., "Catalytic Hydrogenation of Dihydroxyacetone".

*Primary Examiner*—J. E. Evans
*Attorney, Agent, or Firm*—Brooks Haidt Haffner & Delahunty

[57] ABSTRACT

This invention relates to a process for synthesis of glycerol from formaldehyde, wherein formaldehyde under substantially anhydrous condition is self-condensed in a catalytic step is dihydroxyacetone which is separated from the self-condensation catalyst and hydrogenated catalytically to glycerol.

The feature of the invention is to have less than 0.4% w/w of water in the self-condensation reaction mixture thereby improving the process to produce glycerol in commercially viable rates and yields.

23 Claims, No Drawings

SYNTHESIS OF GLYCEROL FROM FORMALDEHYDE

This application is a continuation, of application Ser. No. 07/236,651, filed Aug. 25, 1988 now abandoned.

The present invention relates to a process for the synthesis of glycerol from formaldehyde.

Glycerol is a valuable raw material for the production of various esters, printing inks, foodstuffs, in antifeezes, as a moistening agent in tobacco and in soaps and for producing nitroglycerine.

Hitherto glycerol has been produced from animal and vegetable oils and fats, in which it occurs as the glyceryl ester of mainly palmitic, stearic and oleic acids, by hydrolysis or hydrogenolysis. Glycerol is also obtained in large quantities as a by-product in the manufacture of saop, and this is till a commercial source of glycerol. Another method of preparing glycerol is the fermentation of glucose to which sodium sulphite has been added (the yield is 20-25%) Glycerol can also be produced from propylene which is converted to allyl chloride, thereafter into allyl alcohol, then into a monochlorohydrin which is finally hydrolysed into glycerol.

A new process is to add osmium tetroxide and hydrogen peroxide to acrylaldehyde; this produces glyceraldehyde which is then catalytically hydrogenated to glycerol.

Thus, apart from two relatively expensive and complicated synthetic routes, the primary commerical source of glyceol is still as a by-product from soap and fatty alcohol manufacture.

It is an object of the present invention to devise a simple synthetic route to glycerol from formaldehyde.

Matsumoto, T. et al in Journal of the American Chemical Society, 1984, 106, pp 4829-4832 describe a method of synthesising dihydroxy acetone from paraformaldehyde. ICI's U.S. Pat. No. 4,024,193 describes, amongst others, hydrogenation of pure dihydroxy acetone to glycerol using a homogeneous catalyst system. EP 245976 (ICI) describes a process for isolating dihydroxyacetone from a self condensation reaction but uses low formaldehyde to catalyst ratio.

In all these prior art processes, the self condensation stage has been carried out using formaldehyde which ahs significant quantities of water, usually 2-7% w/w, or, use relatively low formaldehyde to catalyst ratios. Hence productivity and yields have been low rendering the synthesis of a product such as glycerol commercially non-viable.

It has now been found that formaldehyde can be converted into dihydroxy acetone and then hydrogenated to glycerol in significant rates and yields to make the integrated process commercially viable.

Accordingly, the present invention is a process for producing glycerol from formaldehyde said process comprising:

(a) self-comdensing formaldehyde in the presence of a condensation catalyst system comprising a salt of a hterocyclic nitrogen containing compound and a proton abstractor in a substantially anhydrous liquid reaction medium to form dihydroxy acetone or dimers or oligomers thereof, under the following conditions:
  (i) the initial reaction solution contains at least 10% w/w of formaldehyde,
  (ii) the formaldehyde to catalyst molar ratio in the initial reaction mixture is at least 150:1,
  (iii) the reaction temperatures is from 20°-200° C., and
  (iv) the reaction pressure is controlled so as to maintain the reactants and the solvent in the reaction mixture in a liquid phase;

(b) separating the dihydroxyacetone so formed from the condensation catalyst to render it substantially free of sulphur, nitrogen and halogen containing components; and (c) hydrogenating the dihydroxyacetone, dimers and oligomers thereof obtained from step (b) in the presence of a hydrogenation catalyst.

By "substantially anhydrous liquid reaction medium" is meant that the solution of formaldehyde and the self condensation catalyst system contains less than 0.4% w/w of water. It is preferable that the water content is less than 0.1% w/w. This may be achieved by using essentially dry formaldehyde as the reactant. Formaldehyde is normally sold commercially as alcoform, paraformaldehyde or as an aqueous solution thereof. Paraformaldehyde typically contains about 7% w/w water and even the best grades contain about 2% w/w water. The feature of the present invention is to use dry formaldehyde reactant, whether from a commercial source or dired further, prior to use in the reaction in order to reduce the water content of the formaldehyde to below 1% w/w.

As regards step (a) formaldehyde may be added in monomeric, oligomeric or polymeric form. In monomeric form it may be added either as formaldehyde gas or as a solution of formaldehyde in an organic solvent, suitably an alkanol, for example methanol, ethanol or propanol, butanol, cyclohexanol, methylisobutyl carbinol, 2-ethyl hexanol, glycols, polyols such as glycerol or a mixture thereof. It is possible to use glycerol as the solvent/reaction medium for step (a) which has the advantage that no solvent separation stage is required prior to subsequent processing.

The salt of a heterocyclic nitrogen containing compound is suitably a thiazolium salt or an imidazolium salt. It is preferably an aliphatic, aromatic or a heterocyclic thiazolium salt. Specific examples of such salts include the halides especially the bromide and iodide salts. Of these the 3-methyl benzothiazolium iodide, 3-ethylbenzothiazolium bromide, 3-laurylbenzothiazolium bromide, 3-isopropylbenzothiazolium bromide, 3-butylbenzothiazolium bromide and 3-ethyl thiazolium bromide are specific examples. The N-containing heterogeneous base is chosen so as to offer an optimum combination of activity in stage (a) ane ase of separation from the dihydroxyacetone in stage (b). An alternative approach is to chemically bond the catalyst to a polymeric backbone or to an inorganic oxide support to facilitate separation thereof from the reaction products.

Likewise the proton abstractor should offer an optimum combination of giving an active condensation catalyst system for the self condensation reaction and ease of separation from the dihydroxyacetone in stage (b). Examples of such proton abstractors include:

(i) the amines, which may be primary, secondary, or tertiary and can be aliphatic, alicyclic, aromatic or heterocyclic (ii) the compounds containing a basic oxygen atom such as those derivable by the reaction of an inorganic oxide, an amine or a phosphine with an epoxide, or (iii) a metal alkoxide.

Where an amine is used as the proton abstractor, ease of separation can be enhanced by suitable selection of the hydrocarbon groups of amine. Specific examples of the amines includes triethyl amine, imidazole, pyridine, pyrimidine, piperazine or the strong amidine or guanidine type bases e.g. 1,5,7-triazabicyclo-[4.4.0]dec-5-ene (TBD).

The phosphines referred to in (ii) above may be alkyl or aryl phosphines or mixed alkyl/aryl phosphines. Specific examples of the phosphines include triphenyl phosphine and triethyl phosphine. Whether phosphines or amines are used, such proton abstractors can be supported on or immobilized by e.g. an ion-exchange resin or silica.

Specific examples of epoxidised bases include ion-exchange resins such as the reaction product of butene oxide and Amberlyst A21 resin (Registered Trade mark) and the epoxidised metal oxides such as the reaction product of butene oxide and gamma alumina.

The condensation catalyst system should be such that the chemical equivalent ratio of the salt of a heterocyclic nitrogen containing compound to the proton abstractor is from 1:1 to 10:1. Preferably, the two are present either in chemically equivalent ratios or in ratios where the salt of a heterocyclic nitrogen containing compound is in a marginal excess. Where a weak base such as an imidazolium salt is used, such a salt may be present in a substantial excess without adversely affecting the self condensation reaction.

The relative molar ratios of formaldehyde to the condensation catalyst components in the initial reaction mixture for the self-condensation reaction is at least 150:1. Assuming that the thiazolium salt and the proton abstractor are present in chemically equivalent amounts in the condensation catalyst system, the molar ratio of formaldehyde to one of the catalytic components should be as high as is practicable and may vary from 150:1 to 10000:1.

The liquid reaction medium for the self condensation step is suitably a solvent or mixtures of solvents capable of dissolving at least one of formaldehyde and the condensation catalyst system. In a homogeneous system clearly the solvent will dissolve both. Specific examples of the solvents that can be used include the aliphatic alcohols, e.g. ethanol, n-propanol, isopropanol, the butanols, methylisobutyl carbinol and 2-ethyl hexanol; glycols and polyols, e.g. glycerol; cycloaliphatic alcohols, e.g. cyclohexanol; esters; ethers such as tetrahydrofuran, dioxan and glycol ethers such as, e.g. diethyl glycol dimethyl ether; aprotic solvents such as dimethyl sulphoxide and dimethl formamide; hydrocarbons, especially alkanes such as heptane; and mixtures of two or more of these solvents.

The self condensation of formaldehyde is carried out at a temperature from 20°-200° C., preferably from 80°-170° C. It will be appreciated that the reaction is exothermic and hence reactions initiated within this range may during the reaction exceed the preferred upper limit of 170° C. specified herein. The reaction pressure may be ambient or elevated provided that the pressure is controlled to maintain the reactants and/or solvents substantially in the liquid state.

For example, when using a formaldehyde to a condensation catalyst mole ratio of 150:1 and 2-ethylhexanol as solvent, at a temperature of about 130° C., the reaction time is suitably about 10 minutes.

As regards step (b), it is an essential feature of the invention to separate the dihydroxy acetone from the self-condensation catalyst used in step (a) above. The self condensation catalyst system has a tendency to poison the hydrogenation catalyst used in the second stage of the reaction. In order to minimize this effect, the reaction products of step (a) are rendered substantially free of the self condensation catalyst prior to the hydrogenation step (c). The sulphur, nitrogen and halogen containing components of the self condensation catalyst system should be removed from the process stream. Typically, the degree of removal should be such that the process stream contains not more than 10 ppm by weight of either sulphur, nitrogen or halogen.

The self condensation product containing dihydroxy acetone as such, as a dimer thereof or as a mixture of the two can be separated from the catalyst components by conventional means e.g. by one or more of the following: precipitation, dialysis, liquid-liquid extraction, ion exchange, membrane separations such as hyperfiltration, vacuum distillation, e.g. steam stripping, and the use of adsorbent materials.

In the case of certain solvents, e.g. alcoholic solvents such as isopropanol and 2-ethyl hexanol, used in the self-condensation stage, the dihydroxy acetone formed can be separated from the reaction mixture simply by cooling whereby the dihydroxy acetone preiciptates. The remaining liquid phase can be optionally recycled to the condensation reactor or further processed in the separation stage. Precipitation can be made to occur so as to recover a greater proportion of the dihydroxyacetone or its dimer than is achieved simply by cooling. One method is to reduce the volume of the solvent present by distillation and then cool the remaining solution. An alternative approach is to remove essentially all of the solvent to give a solid or a viscous liquid phase. This phase is then redissolved in a solvent from which dihydroxyacetone or its dimer can be readily precipitated either by cooling or by the addition of a second liquid component such as e.g. additions of diethyl ether or 2-ethylhexanol to a solution of the viscous phase in acetone.

Under certain temperature or dihydroxyacetone concentration regimes it is possible to substantially separate the dihydroxyacetone from the reaction solvent as a liquid phase precipitation. A dihydroxyacetone rich liquid phase can thus be removed for further processing leaving a solvent rich phase for recycle to stage (a).

If it is intended to use liquid-liquid extraction as the separation method, then the nitrogen containing heterocyclic base and amine catalyst system used in stage (a) should be chosen with a consideration of the solvent and extractant to be used. For example, water can be used as the extractant to preferentially extract dihydroxyacetone from reaction solvents such as 2-ethyl hexanol. In this case, the efficiency of separation of dihydroxyacetone can be improved by using as catalyst a nitrogen containing heterocyclic base and amine both bearing large aliphatic grups thereby enhancing the partition of teh catalyst system into the organic phase. In a water/2-ethylhexanol liquid separation for example, retention of the amine components in the 2-ethylhexanol phase is aided by the presence of at least one hydrophobic group in the amine.

Adsorbent materials may also be used to remove the catalyst system from the reactant product either alone or in combination with any one of the above methods. Typical adsorbents include activated carbons, alumina, silica, metal oxides, supported metals on carbon or metal oxide and ion exchange resins. With certain adsorbent materials, it can be advantageous to regenerate the absorbent, for example by heating the absorbent in a suitable atmosphere such as hydrogen, steam or air. Adsorbent treatments are particularly suitable for use in combination with a treatment such as liquid-liquid extraction.

It is another feature of the invention that provided the sulphur, nitrogen and halogen containing components are substantially removed from the reaction products of step (a), the remaining products containing crude dihydroxy acetone need not be further purified prior to use in the hydrogenation step (c).

As regards the hydrogenation step (c), the dihydroxyacetone can be hydrogeanted in the presence of a hydrogenation catalyst and hydrogen. The hydrogenation catalyst may be a heterogeneous or a homogeneous hydrogenation catalyst.

Where the catalyst is a heterogeneous hydrogenation catalyst it is suitably a finely divided or a supported Group VIII metal. For example such a catalyst may be nickel, Raney nickel or ruthernium supported on a support inert under the reaction conditions e.g. carbon or graphite, or a copper chromite type catalyst. Where the hydrogenation catalyst is a homogeneous catalyst, such a catalyst is soluble in the liquid reaction medium and is suitably a compound or mixture of compounds containing a noble metal moiety (i) and a moiety (ii) of the formula $XR_3$ wherein X is either phosphorus, arsenic or antimony and the groups R are independently either hydrogen or hydrocarbyl or substituted hydrocarbyl group. Throughout this specification the term noble metal means platinum, palladium, rhodium, ruthenium, iridium or osmium. Of the noble metals, palladium, platinum, rhodium and ruthenium are preferred. Preferably X in the formula is phosphorus. The group R in the formula is preferalby a hydrocarbyl or substituted hydrocarbyl group. Suitable hydrocarbyl groups include alkyl groups, cycloalkyl groups and aryl groups, which may be substituted or unsubstituted. The catalyst may suitably combine the moieites (i) and (ii) in a single compound, for example as the compound $RhCl(PPh_3)_3$ or the compound $Ru(H)(OAc)PPH_3)_3$. Alternatively, the moieties (i) and (ii) may be added in the form of separate compounds for example as $RhCl_2$ and $PPh_3$ to form the catalyst in situ.

Where the catalyst is a homogeneous hydrogenation catalyst, particularly when this takes the form of a single compound, it may be supported on a suitable support. Suitable supports include organic polymers, for example polystyrene containing the appropriate functional moiety (ii).

Hydrogen is readily available on a commercial scale. It may be used in a commercially available form or may, if desired, be further purified. The hydrogen partial pressure may suitably be in the range from 10 to 30,000 KPa, preferably from 100 to 5000 KPa.

The hydrogenation step (c) may suitably be accomplished at elevated temperature, suitably in the range from ambient to 150° C., preferably from 40° to 150° C., most preferably from 40° to 120° C.

The liquid reaction medium for the hydrogenation step is suitably a solvent capable of dissolving the hydrogenation reactants and, in the case of a homogeneous reaction, the catalysts. Suitable solvents include, but are not restricted to, alcohols, water, ethers and mixtures of one or more of these. The particular solvent of preference may be advantageously the same as that chosen for the self condensation step (a) and the catalyst removal method of step (b).

The hydrogenation step (c) may suitably be carried out batchwise or continuously, preferably continuously.

For batch operation the duration of the hydrogenation reaction will vary with the type and concentration of the hydrogenation catalyst, the hydrogen partial pressure and with the nature of the product being hydrogenated, i.e. whether crude or pure or whether the reaction is carried out in situ. The glycerol product formed upon hydrogenation can be purified and recovered by methods well known in the art. A suitable method of purification is vacuum distillation. If required post treatments known to those skilled in the art may be used. Such treatments include, but are not restricted to, passage over a carbon bed and treatment with a bleaching agent.

The present process is clearly simpler and less expensive to operate than the synthetic processes used hitherto. The raw materials are easily available and the products easily separated and purified.

The present invention is further illustrated with reference to the following Examples.

EXAMPLES 1-3

The following examples demonstrate that methanol is a suitable solvent for the reaction. The reaction in each case was carried out in a stainless steel tubular reactor, length 20 m, volume 62 ml, equipped with a variable speed pump, a water condenser and a pressure regulating valve.

Formaldehyde gas, produced by thermal decomposition of paraformaldehyde solid was dried over $P_2O_5$ and bubbled into dry solvent. To the resulting solutions were added 0.1584 g 3-ethylbenzothiazolium bromide and 0.336 g 1,5,7-triazabicycl[4.4.0]dec-5-ene (TBD) per 100 g solution.

The formaldehyde concentrations were determined by titration using sodum bisulphite/iodine solutions. Dihydroxyacetone concentrations were determined by high pressure liquid chromatography.

Results obtained are given below in Table 1.

TABLE 1

| Example | Initial CH$_2$O:catalyst (molar) | Initial CH$_2$O by % wt | Solvent | Initial Water % w/w | Oven Temp °C. | Residence Time in mins | DHA Conc in Product solution by % wt |
|---|---|---|---|---|---|---|---|
| 1 | 146 | 10.5 | 10:1 DMF/MeOH | 0.10 | 120 | 8.1 | 7.4 |
| 2 | 147 | 10.6 | MeOH | 0.12 | 141 | 7.5 | 9.8 |
| 3 | 288 | 20.7 | MeOH | 0.12 | 141 | 20.9 | 17.1 |

DHA - Dihydroxyacetone
DMF - Dimethylformamide

EXAMPLES 4-7

Examples 4-7 demonstrate the use of compounds containing basic oxygen atoms, derived by the reaction of a basic ion exchange resin (amberlyst A21) or an inorganic oxide with an epoxide, as proton abstactors.

EXAMPLE 4

A 100 ml (99.4 g) of formaldehyde (9.04% w/w) dissolved in DMF/methanol (10:1) was charged to a 3-necked round bottomed flask together with 0.284 g of Amberlyst A21 (Registered Trade Mark, predried in vacuo, at room temeprature over 24 hours) and 0.345 g but-1-ene oxide. The flask equipped with a condenser and a magnetic follower, was heated to 60° C. with stirring for one hour. The contents were then heated to 120° C. and 0.584 g 3-ethylbenzothiazolium bromide added and the reaction monitored by g.l.c. (see Table 2 below).

The initial water content by Karl Fisher was 0.07% w/w.

The initial formaldehyde:thiazolium salt molar ratio was 96:1.

EXAMPLE 5

The procedure of Example 4 was repeated using 1 g gamma alumina (predried) instead of Amberlyst A21 (Registered Trade Mark). The reaction was monitored by g.l.c. (see Table 2 below).

The initial water content by Karl Fisher was 0.16% w/w.

The initial formaldehyde:thiazolium salt molar ratio was greater than 80.1.

EXAMPLE 6

The procedure of Example 4 was repeated using 1 g silica (predried) instead of Amberlyst A21 (Registered Trade Mark). The reaction was monitored by g.l.c. (see Table 2 below).

The initial water content by Karl Fisher was 0.07% w/w.

The initial formaldehyde:thiazolium salt molar ratio was 78.1

EXAMPLE 7

The procedure of Example 4 was repeated using 1 g of powdered 3A molecular sieves (predried) instead of Amberlyst A21 (Registered Trade Mark). The reaction was monitored by g.l.c. (see Table 2 below).

The initial water content by Karl Fisher was 0.02% w/w.

The initial formaldehyde:thiazolium salt molar ratio was 175.1

TABLE 2

| Example | 4 | 5 | 6 | 7 |
|---|---|---|---|---|
| Support | Amberlyst A21 | gamma alumina | silica | 3A molecular sieves |
| Run time* (mins) | 60 | 60 | 60 | 60 |
| Dihydroxy-acetone (g) | 6.83 | 4.6 | 5.96 | 7.62 |

*t = 0 time of addition of 3-ethyl benzothiazolium bromide.

EXAMPLE 78

1.201 g 3-ethylbenzothiazolium bromide and 0.691 g 1,5,7-triazabicyclo[4.4.0 dec-5-ene were dissolved in 370.9 g of a stock solution of n-propanol, formaldehyde (10.8% w/w) and water 0.18% w/w). This solution was reacted in a flow reactor (feed rate 10 ml/h, 97°-98° C., heating time 10 minutes), cooled and passed down an ion-exchange column (Amberlyst 15H (Registered Trade Mark), 20 g, predried), collected over a 20 hours period and the solvent removed on a rotary evaporator. The sample of yellow oil thus obtained was diluted with isopropanol to 75 ml. 25 ml of this solution together with 0.5 g Raney nickel where charged to a Fischer Porter tube. The hydrogenation was carried out at 100° C., 590 KPa hydrogen, for 6 hours, then cooled and the yellow solution analysed by g.l.c. It was found to contain glycerol (ca 2.5% wt).

As a comparative test when hydrogenation of the product from the self-condensation reaction was attempted before treatment with ion-exchange resin, no glycerol was obtained.

The use of a flow reactor enables shorter reaction times to be achieved minimising decomposition of dihydroxyacetone which has been observed with longer reaction times (e.g. see Example 15).

EXAMPLES 9-13

Dry formaldehyde gas, produced by the prior thermal decomposition of paraformaldehyde solid (14.4 g) and passing of this gas stream through a heated granular phosphorous pentoxide bed, was slowly bubbled into a reaction flask containing dimethyl formamide (84.55 g) and methanol (8.45 g) maintained at 120° C. Once the addition was complete, the formaldehyde generator was isolated and the contents of the reaction flask analysed for water (by Karl Fischer) and formaldehyde (by gas chromatography). The water level was then adjusted, by addition of deionised water, to the desired level.

The catalyst precursors 3-ethylbenzothiazolium bromide (0.584 g) and 1,5,7-triazabicyclo[4.4.0]-dec-5-ene (0.336 g) were dissolved in a 5 ml aliquot of hot solution and syringed into the reaction flask. From the time of catalyst addition samples were taken at regular intervals for dihydroxyacetone and formaldehyde analysis. These examples demonstrate that the incremental presence of water is detrimental to catalyst activity and dihydroxyacetone production. The results are shown in Table 3 below.

TABLE 3

| Example | Initial Water Level % w/w | Initial Formaldehyde:catalyst ratio (molar) | Reaction Time (mins) | DHA % w/w | Formaldehyde % w/w |
|---|---|---|---|---|---|
| 9 | 0.4 | 137:1 | 10 | 3.627 | 3.847 |
| 10 | 0.2 | 145:1 | 10 | 4.082 | 1.877 |
| 11 | 0.15 | 173:1 | 10 | 4.797 | 1.426 |
| 12 | 0.12 | 165:1 | 10 | 6.574 | 0.937 |
| 13 | 0.06 | 150:1 | 10 | 7.648 | 2.120 |

DHA - Dihydroxyacetone

EXAMPLE 14

A formaldehyde solution (23.9% wt CH2O, less than 0.1% wt H2O) was prepared by heating together paraformaldehyde and 2-ethylhexanol to 100° C. and then treating the resulting solution with 3A molecular sieves to remove water.

The reactor feed solution was prepared by dissolving 3-ethylbenzothiazolium bromide (0.6 mmol) and triethylamine (0.06 mmol) in 200 g of formaldehyde stock solution. The formaldehyde to catalyst mole ratio was 2656:1.

The reaction was carried out in a pressurzied (1000 KPa) stainless teel tubular reactor (glass bead packed bed, void volume=2.8 ml) equipped with a feed pot, a variable speed pump, a water condenser and a product tank. The bed temperture (140° C.) was monitored by means of a central thermowell equipped with three thermocouples (top, middle, bottom of bed). The formaldehyde concentrations were determined by gas chromatography. The water level was determined by Karl Fischer and the dihydroxyacetone (DHA) by high pressure liquid chromatography. The results are presented below in Table 4.

TABLE 4

| Reaction Time (mins) | % CH2O wt/wt | % DHA wt/wt | Conversion % | Selectivity to DHA % |
|---|---|---|---|---|
| 4 | 16.7 | 6.7 | 30 | 93 |

EXAMPLE 15

The method of Example 14 was followed except that iso-propanol was used instead of 2-ethylhexanol. The initial water content was 0.07% (Karl Fischer). The initial formaldehyde content was 40% (by gas chromatography). The initial formaldehyde:catalyst ratio (molar) was 1115:1.

The results presented below in Table 5 demonstrate that isopropanol is also a suitable reaction solvent.

TABLE 5

| Reaction Time (mins) | Conversion % (CH2O) | Selectivity to DHA % |
|---|---|---|
| 1 | 36 | 88 |
| 3.5 | 51 | 71 |
| 7 | 56 | 69 |

DHA - Dihydroxyacetone

EXAMPLE 16

The method of Example 15 was followed. The product mixture was allowed to cool to room temperature. The dihydroxyacetone (DHA) precipitate was washed with cold isopropanol and dried in a stream of nitrogen. 0.8 g of the dihydroxyacetone (confirmed by HPLC) was dissolved in iso-propanol (6 g), heated to 100° C. with 0.5 g Raney Nickel and 590 KPa hydrogen in a Fischer Porter tube. After 2 hours the reaction was allowed to cool to room temperature. Analysis by gas chromatography and HPLC demonstrated that 100% conversion of dihydroxyacetone had occured to give glycerol (80% yield). This demonstrates that purification from the catalyst can be achieved by crystallisation of the dihydroxyacetone from the reaction solvent.

EXAMPLES 17-19

Examples 17-19 demonstrate the use of liquid-liquid extraction, ion exchange resin and carbon adsorbents to separate the self-condensation catalyst from dihydroxyacetone (DHA).

EXAMPLE 17

5 g dihydroxyacetone (DHA), 0.5 g 3-ethylbenzothiazolium bromide and 0.1 g triethylamine base were dissolved into 100 g of a stock solution (dried to less than 0.5% w/w water by molecular sieve) of 2ethylhexanol and formaldehyde (2.5% w/w). The mixture was allowed to stand overnight before 50 ml of the organic phase was extracted with 10 ml of deionised water (15 mins contact time, 30 mins settling time). Following partition, the organic phase was similarly extracted a further two times with fresh deionised water to give a total of three successive extractions. Analysis, by HPLC, showed the original organic phase to contain 4.7% w/w DHA and the final organic phase to contain less than 011% w/w DHA respectively. Hence, 98% DHA recovery was achieved by three successive extractions with water. This system, using a ratio of organic phase to aqueous phase of 5:1 (v/v), gave recovery into the organic phase of 90%, 54% and 8% for sulphur, nitrogen and bromide respectively. Elemental analysis for bromide and sulphur was achieved using combustion/ion chromatography whilst nitrogen was analysed by oxidative pyrolysis/chemiluminescence.

EXAMPLE 18

The procedure of Example 17 was repeated except that 0.5 g of 3-laurylbenzothiazolium bromide was used instead of 0.5 g of 3-ethylbenzothiazolium bromide as the catalyst. Extraction with deionised water gave a 93% recovery of njitrogen into the 2-ethylhexanol phase. Hence, 3-laurylbenzothiazolium component of the catalyst partitions better into the organic phase compared to 3-ethylbenzothiazolium component.

Thus, dihydroxyacetone (DHS) and bromide component preferentially partition into water during 2-ethylhexanol/water extraction.

EXAMPLE 19

The bromide component from the product of Example 17 was removed using the following procedure. The aqueous layer from Example 17 was pumped through a vertical column (10 mm internal diameter, LHSV=4) containing 10 mls of either an anionic ion exchange resin (for example, Bayer E1338/88) or a carbon adsorbent (for example, Sutcliff-Speakman Carbon 607). Bromide ions were detected by precipitation on addition of silver nitrate solution (0.1M). Precipitation occurred before but not after the ion exchange/adsorbent treatment.

EXAMPLE 20

To a glass Fischer Porter tube was charged, a magnetic follower, Ru(H)(OAc)(PPh3)3 (0.12 g), dihydroxyactone (1 g) and iso-propanol (6 g). The tube was purged with hydrogen and pressurised to 590 KPa with hydrogen. The tube was heated with stirring, in an oil bath to 100° C. when, judged by gas uptake, reaction commenced. The pressure was maintained at 500-700 KPa by addition of more hydrogen gas as necessary. Gas uptake ceased after 180 minutes. Analysis of the cooled product by gas liquid chromatography (glc)

indicated that essentially complete conversion of dihydroxyacetone to glycerol had taken place.

EXAMPLE 21

The procedure of Example 20 was repeated using 0.5 g of RhCl(PPh$_3$)$_3$ instead of Ru(H)(OAc)(PPh$_3$)$_3$. Gas uptake ceased after 1 hour and 45 minutes. The yield of product was 100% baswed on glc analysis.

EXAMPLE 22

The procedure of Example 20 was repeated using 0.5 g of RhCl(PPh$_3$)$_3$ instead of Ru(H)(OAc)(PPh$_3$)$_3$. Gas uptake ceased after 2 hours. The yield of product was 100% based on glc analysis.

EXAMPLE 23

To a glass Fischer Porter tube was charged, a magnetic follower, Raney nickel (0.5 g), dihydroxyacetone (1 g) and isopropanol (6 g). The system was assembled, purged with hydrogen, and pressurized to 590 KPa with hydrogen. The tube was heated, with stirring, in an oil bath to 100° C. when, as judged by gas uptake, reaction commenced. The pressure was maintained at about 450-590 KPa by addition of more hydrogen gas as necessary. Gas uptake ceased after 50 minutes. Analysis of the cooled product by gas-liquid chromatography (glc) indicated that essentially complete conversion of dihydroxyacetone to glycerol had taken place.

EXAMPLE 24

The procedure of Example 23 was repeated using 0.5 g of 5% ruthenium on carbon instead of Raney nickel. Gas uptake ceased after 1 hour and 25 minutes. The yield of product was 98% based on glc analysis.

Comaparative Test (not according to the invention)—Hydrogenation in the presence of condensation catalyst components The procedure of Example 23 was repeated using 0.17 g of triethylamine and 0.41 g of 3-ethyl benzothiazolium bromide in addition to the Raney nickel. No gas uptake was observed, no glycerol was formed (glc analysis).

EXAMPLES 25-28

Hydrogenation of dihydroxyacetone (DHA) was carried out over a 50% Ni/SiO$_2$:Al$_2$O$_3$ catalyst (Sud-Chemie G134 A RS 1/32" extrusions) in a 0.1 dm$^3$ semi-technical continuous unit. For experiments at 1710 KPa, 100 mls of catalyst was loaded into a stainless steel reactor of interval dimeter 2.5 mm which could be heated in three separate zones (top, catalyst bed, bottom). The catalyst was then activated by heating, at 1710 KPa, in 50:50 stream of H$_2$:N$_2$ to 200° C., at a rate of 15° C./hr, and then holding for 6 hours, After activation, the catalyst was cooled in hydrogen to the desired reaction temperature. A mixture of 7-8 wt % DHA in iso-propyl alcohol and hydrogen was then passed over the catalyst, and the pressure was adjusted to the required value by means of an air operated automatic pressure control valve.

Catalyst performance was assessed by carrying out 10 hour mass balances preceded by 10 hour pre-runs to allow steady-state conditions to be attained. Product vapours, gases and liquids were sampled, after gas/liquid separation, and analysed by off-line gas-liquid chromatography and by high performance liquid chromatography. The temperatures were measured by means of thermocouples inverted into the top, middle and bottom of the catalyst bed.

For the purposes of the examples, conversion and selectivities have been calculated as respectively, the proportion of DHA reacted, and the proportion of the reacted DHA which is converted to glycerol.

Definitions

LHSV = Liquid Hourly Space Velocity = liters liquid feed per liter of catalyst.

Productivity = kg DHA converter to glycerol per kg catalyst per hour.

7 wt % DHA in isopropanol was hydrogenated over a silica-alumina catalyst (Sud Chemie G-134 A RS). The LHSV was varied from 0.5 to 2.0, the ratio of hydrogen to DHA was ca 30:1 molar and the pressure was 1710 KPa. The catalyst was activated as previously described and the results are collated in the following Table 6.

The greatest selectivity was obtained at LHSV = 2.

TABLE 6

| HYDROGENATION OF DHA ON THE 0.1 dm$^3$ STU | | | | |
|---|---|---|---|---|
| Example | 25 | 26 | 27 | 28 |
| 1. Temperature | 100.00 | 100.00 | 100.0 | 100.00 |
| 2. LHSV | 0.50 | 1.00 | 1.5 | 2.00 |
| 3. Pressure | 290.00 | 290.00 | 290.0 | 290.00 |
| 4. H$_2$:DHA | 30.00 | 30.00 | 30.0 | 30.00 |
| 5. Conversion | 100.00 | 100.00 | 100.0 | 100.00 |
| 6. Glycerol Sel | 75.00 | 85.00 | 87.0 | 90.00 |
| 7. Productivity | 0.04 | 0.07 | 0.1 | 0.13 |

DHA - dihycroxyacetone

We claim:

1. A process for producing glycerol from formaldehyde, said process comprising:
   (a) self-condensing formaldehyde in the presence of a condensation catalyst system comprising a slat of a heterocyclic nitrogen containing compound and a proton abstractor in a substantially anhydrous liquid reaction medium containing less than 0.4% w/w water to form dihydroxy acetone or dimers or oligomers thereof, under the following conditions:
      (i) the initial reaction solution contains at least 10% w/w of formaldehyde,
      (ii) the formaldehyde to catalyst molar ratio in the initial reaction mixture is at least 150:1,
      (iii) the reaction temperature is from 20°-200° C., and
      (vi) the reaction pressure is controlled so as to maintain the reactants and the solvent in the reaction mixture in a liquid phase;
   (b) separating the dihydroxy acetone or dimers or oligomers thereof so formed from the condensation catalyst to render it substantially free of sulfur, nitrogen and halogen containing components; and
   (c) hydrogenating the dihydroxy acetone, dimers and oligomers thereof obtained from step (b) in the presence of a hydrogenation catalyst.

2. A process according to claim 1 wherein the formaldehyde is used in its monomeric form and is added either as formaldehyde gas or as a solution of formaldehyde in an organic solvent.

3. A process according to claim 1 wherein the salt of a heterocyclic nitrogen containing compound is a thiazolium salt or an imidazolium salt.

4. A process according to claim 3 wherein the thiazolium salt in the condensation catalyst system is an aliphatic, aromatic or a heterocyclic thiazolium salt.

5. A process according to claim 3 wherein the thiazolium salt is 3-methyl benzothiazolium iodide, 3-ethylbenzothiazolium bromide, 3-isopropylbenzothiazolium bromide, 3-butylbenzothiazolium bromide, 3-laurylbenzothiazolium bromide or 3-ethyl thiazolium bromide, 6. A process according to claim 1 wherein the proton abstractor is
   (i) an amine, which is primary, secondary, or tertiary and which is aliphatic, alicyclic, aromatic or heterocyclic, or,
   (ii) a compound containing a basic oxygen atom of the type derivable by the reaction of an inorganic oxide, an amine or a phosphine with an epoxide, or,
   (iii) a metal alkoxide.

7. A process according to claim 6 wherein the phosphine in (ii) is an alkyl or an aryl phosphine or mixed alkyl/aryl phosphines.

8. A process according to claim 6 wherein the amine is selected from triethylamine, lauryl amine, imidazole, pyridine, pyrimidine, piperazine and the amidine and guanidine type bases.

9. A process according to claim 6 wherein the epoxidised bases in (ii) are selected from the reaction product of butene oxide and Amberlyst A21 resin, and the reaction product of butene oxide and gamma alumina.

10. A process according to claim 1 wherein the chemical equivalent ratio of the salt of a heterocyclic nitrogen containing compound to the proton abstractor varies from 1:1 to 10:1.

11. A process according to claim 1 wherein for the self-condensation reaction the relative molar ratios of formaldehyde to the condensation catalyst components comprising the salt of a heterocyclic nitrogen containing compound and the proton abstractor present in substantially chemical equivalent amounts, is from 150:1 to 10000:1.

12. A process according to claim 1 wherein the liquid reaction medium for the self-condensation step is a solvent or mixtures of solvents capable of dissolving at least one of formaldehyde and the condensation catalyst system.

13. A process according to claim 12 wherein the solvent is selected from aliphatic alcohols, cycloaliphatic alcohols, glycols, polyols, esters, ethers, aprotic solvents, hydrocarbons, and mixtures of two or more of these solvents.

14. A process according to claim 1 wherein the self condensation of formaldehyde is carried out at a temperature from 80°–170° C.

15. A process according to claim 1 wherein the self condensation product containing dihydroxy acetone as such, as a dimer thereof or as a mixture of the two is separated from the catalyst components by using a method selected from the group consisting of ion-exchange technique, dialysis, liquid-liquid extraction, precipitation, vacuum distillation and adsorption.

16. A process according to claim 1 wherien the catalyst for a heterogeneous hydrogenation reaction is (i) a finely divided or a supported Group VIII metal or (ii) copper chromite.

17. A process according to claim 1 wherein the catalyst for a homogeneous hydrogenation reaction is soluble in the liquid reaction medium and is a compound or mixture of compounds containing (i) a noble metal moiety and (ii) a moiety of the formula $XR_3$ wherein X is either phosphorus, arsenic or antimony and the groups R are independently either hydrogen or hydrocarbyl or substituted hydrocarbyl groups.

18. A process according to claim 17 wherein the groups R are alkyl groups, cycloalkyl groups or aryl groups, which may be substituted or unsubstituted.

19. A process according to claim 17 wheren the moieties (i) and (ii) are combined in a single compound.

20. A process according to claim 19 wherein the single compound is $RhCl(PPh_3)_3$ or $Ru(H)(OAc)(PPh_3)_3$.

21. A process according to claim 1 wherein hydrogen partial pressure for step (c) is in the range from 10 to 30,000 Kpa.

22. A process according to claim 1 wherein the hydrogenation step (c) is carried out at a temperature from ambient to 150° C.

23. A process according to claim 1 wherein the steps (a), (b) and (c) are carried out using the same solvent medium.

* * * * *

UNITED STATES PATENT AND TRADEMARK OFFICE
CERTIFICATE OF CORRECTION

PATENT NO. : 5,097,089

DATED : March 17, 1992

INVENTOR(S) : BENJAMIN P. GRACEY

It is certified that error appears in the above-identified patent and that said Letters Patent is hereby corrected as shown below:

Col. 1, l. 18, correct the spelling of the word "soap".

Col. 1, l. 31, correct the spelling of the word "glycerol".

Col. 1, l. 46, correct the spelling of the word "has".

Col. 1, l. 58, correct the spelling of the word "condensing".

Col. 2, l. 25, correct the spelling of the word "dried".

Col. 2, l. 50, correct the spelling of "and" and "ease".

Col. 3, l. 4, should read "include".

Col. 3, l. 49, should read "e.g. diethylene".

Col. 3, l. 51, correct the spelling of the word "dimethyl".

Col. 4, l. 25, correct the spelling of the word "precipitates".

Col. 4, l. 57, correct the spelling of the word "groups".

Col. 4, l. 58, correct the spelling of the word "the".

Col. 5, l. 2, correct the spelling of the word "adsorbent".

Col. 5, l. 14, correct the spelling of the word "hydrogenated".

Col. 5, l. 21, correct the spelling of the word "ruthenium".

Col. 5, l. 31, should read "groups".

Col. 5, l. 36, correct the spelling of the word "preferably".

UNITED STATES PATENT AND TRADEMARK OFFICE
CERTIFICATE OF CORRECTION

PATENT NO. : 5,097,089
DATED : March 17, 1992
INVENTOR(S) : BENJAMIN P. GRACEY

It is certified that error appears in the above-identified patent and that said Letters Patent is hereby corrected as shown below:

Col. 5, l. 40, correct the spelling of the word "moieties".

Col. 5, l. 42, should read "Ru(H) (OAc) (PPh$_3$)$_3$".

Col. 6, l. 45, should read "1,5,7-triazabicyclo[4.4.0]".

Col. 7, l. 1, should read "(Amberlyst A21)".

Col. 7, l. 9, correct the spelling of the word "temperature".

Col. 7, l. 49, should read "175:1".

Col. 8, l. 10, should read "[4.4.0]".

Col. 9, l. 15, should read "stainless steel".

Col. 10, l. 12, should read "2-ethylhex-".

Col. 10, l. 22, should read "0.1%".

Col. 10, l. 60 and 61, correct the spelling of "dihydroxyacetone".

Col. 11, l. 8, correct the spelling of the word "based".

Col. 11, l. 36, correct the spelling of the word "Comparative".

Col. 11, l. 51, correct the spelling of the word "diameter".

Col. 12, l. 30, correct the spelling of the word "dihydroxyacetone".

UNITED STATES PATENT AND TRADEMARK OFFICE
CERTIFICATE OF CORRECTION

PATENT NO. : 5,097,089

DATED : March 17, 1992

INVENTOR(S) : BENJAMIN P. GRACEY

It is certified that error appears in the above-identified patent and that said Letters Patent is hereby corrected as shown below:

Claim 15, line 6, there should be a period (.) after the word "bromide.".

Claim 16, line 1, correct the spelling of the word "wherein".

Claim 21, line 30, should read "KPa".

Signed and Sealed this

Twentieth Day of July, 1993

*Attest:*

MICHAEL K. KIRK

*Attesting Officer*     *Acting Commissioner of Patents and Trademarks*